US009915597B2

United States Patent
Noda et al.

(10) Patent No.: US 9,915,597 B2
(45) Date of Patent: Mar. 13, 2018

(54) PARTICULATE MATTER MEASUREMENT DEVICE (71) Applicant: ISUZU MOTORS LIMITED, Tokyo (JP)

(72) Inventors: Masafumi Noda, Kawasaki (JP); Mitsuhiro Aso, Yokohama (JP); Tadashi Uchiyama, Kamakura (JP)

(73) Assignee: ISUZU MOTORS LIMITED, Tokyo (JP)

( * ) Notice: Subject to any disclaimer, the term of this patent is extended or adjusted under 35 U.S.C. 154(b) by 449 days.

(21) Appl. No.: 14/768,794

(22) PCT Filed: Feb. 18, 2014

(86) PCT No.: PCT/JP2014/053735
§ 371 (c)(1),
(2) Date: Oct. 29, 2015

(87) PCT Pub. No.: WO2014/129447
PCT Pub. Date: Aug. 28, 2014

(65) Prior Publication Data
US 2016/0047731 A1    Feb. 18, 2016

(30) Foreign Application Priority Data

Feb. 20, 2013    (JP) .................. 2013-031169

(51) Int. Cl.
*F01N 9/00*    (2006.01)
*G01N 15/06*    (2006.01)
(Continued)

(52) U.S. Cl.
CPC ......... *G01N 15/0656* (2013.01); *F01N 9/002* (2013.01); *F01N 11/00* (2013.01);
(Continued)

(58) Field of Classification Search
CPC ............ G01N 15/0656; G01N 15/0618; F01N 9/002; F01N 11/00
See application file for complete search history.

(56) References Cited

U.S. PATENT DOCUMENTS

| | | | |
|---|---|---|---|
| 6,772,584 B2 * | 8/2004 | Chun ................. | B01D 53/9431 422/186.01 |
| 2008/0087007 A1 * | 4/2008 | Konstandopoulos ...................... | B01D 46/0063 60/286 |
| 2011/0005205 A1 * | 1/2011 | Lee .................... | B01D 46/0063 60/277 |

FOREIGN PATENT DOCUMENTS

JP    2012-241643    12/2012

OTHER PUBLICATIONS

Extended European Search Report dated Oct. 6, 2016 in corresponding European Patent Application No. 14754790.5.
(Continued)

*Primary Examiner* — Blake A Tankersley
(74) *Attorney, Agent, or Firm* — Staas & Halsey LLP (57) ABSTRACT

A particulate matter measuring device includes: a diesel particulate filter (DPF) in which upstream side and downstream side openings of multiple cells partitioned by porous partition walls are alternately plugged; a pair of first electrodes received in a pair of first electrode cells arranged diagonally with a central cell therebetween; a pair of second electrodes received in a pair of second electrode cells arranged diagonally with the central cell therebetween; a first connecting member for connecting the first electrodes to each other; a second connecting member for connecting the second electrodes to each other; and a unit that calculates an amount of particulate matter trapped in the DPF on the basis of capacitance between the electrodes. The four cells which are adjacent to each other around the partition walls of the
(Continued)

central cell and sandwiched between the first electrode cells and the second electrode cells are used as measurement cells.

20 Claims, 9 Drawing Sheets

(51) Int. Cl.
*F01N 11/00* (2006.01)
*F01N 13/00* (2010.01)
(52) U.S. Cl.
CPC ........ *F01N 13/008* (2013.01); *F01N 2560/05* (2013.01); *F01N 2560/12* (2013.01); *G01N 15/0606* (2013.01); *Y02T 10/47* (2013.01)

(56) References Cited

OTHER PUBLICATIONS

PCT International Preliminary Report on Patentability dated Aug. 25, 2015 in corresponding International Patent Application No. PCT/JP2014/053735.
Japan Platform for Patent Information, English Abstract of Japanese Publication No. 2012-241643 published Dec. 10, 2012.
International Search Report dated Mar. 25, 2014 in corresponding International Application No. PCT/JP2014/053735.

* cited by examiner

PARTICULATE MATTER MEASUREMENT DEVICE

CROSS-REFERENCE TO RELATED APPLICATIONS

This application is a U.S. National Stage Application, which claims the benefit under 35 U.S.C. § 371 of PCT International Patent Application No. PCT/JP2014/053735, filed Feb. 18, 2014, which claims the foreign priority benefit under 35 U.S.C. § 119 of Japanese Patent Application No. 2013-031169, filed Feb. 20, 2013, the contents of which are incorporated herein by reference.

TECHNICAL FIELD

The present invention relates to a device for measuring particulate matter and, in particular, relates to a device for measuring particulate matter in an exhaust gas emitted from an internal combustion engine.

BACKGROUND ART

A diesel particulate filter (hereinafter referred to as "DPF"), for example, is known as a filter for collecting particulate matter (hereinafter referred to as "PM") in an exhaust gas emitted from a diesel engine. Typically, the DPF includes a number of cells that form lattice-patterned exhaust flow channels defined by partition walls of porous ceramics, and these cells are plugged alternatingly at an upstream side and a downstream side.

The DPF can only collect a limited amount of PM. Thus, upon the amount of accumulated PM reaching a predetermined amount, so-called forced regeneration for burning and removing the accumulated PM needs to be carried out. Therefore, it is desirable to precisely measure the amount of accumulated PM in order to control the forced regeneration.

For example, PATENT LITERATURE 1 discloses a PM sensor that detects an amount of accumulated PM on the basis of an electrostatic capacity (capacitance) of a capacitor formed by a pair of electrodes. The paired electrodes are disposed in a corresponding pair of cells that oppose each other with a measurement cell interposed therebetween. The measurement cell is plugged at its downstream end of the exhaust passage.

LISTING OF REFERENCES

PATENT LITERATURE 1: Japanese Patent Application Laid-Open Publication (Kokai) No. 2012-241643

In the above-mentioned conventional PM sensor, only one capacitor is formed from a pair of electrodes with one cell being interposed between the paired electrodes. Because of this, if it is desired to measure the electrostatic capacity with a larger number of cells, it is necessary to increase the number of electrodes. This can increase the manufacturing cost, and deteriorate the PM collecting capability of the DPF due to the increased number of electrode cells.

SUMMARY OF THE INVENTION

The present invention has been made in view of such a problem, and an object of the present invention is to optimize the electrode arrangement so as to effectively increase the number of capacitors formed between the electrodes.

To achieve the above-mentioned object, a particulate matter measuring device according to the present invention includes a filter that is provided in an exhaust passage of an internal combustion engine and that includes a plurality of cells forming lattice-patterned exhaust flow channels defined by porous partition walls, the cells being plugged alternatingly at an upstream side and a downstream side. One of the cells is defined as a center cell. The particulate matter measuring device also includes a pair of first electrodes disposed in a pair of first diagonal cells that are disposed diagonally across the center cell. The pair of first electrodes are received in the pair of first diagonal cells from an unplugged side. The particulate matter measuring device also includes a pair of second electrodes disposed in a pair of second diagonal cells that are disposed diagonally across the center cell. The first electrodes are not disposed in the pair of second diagonal cells. The pair of second electrodes are received in the pair of second diagonal cells from an unplugged side. The particulate matter measuring device also includes a first connecting member configured to connect the pair of first electrodes to each other, a second connecting member configured to connect the pair of second electrodes to each other, and an accumulation amount calculating unit configured to calculate an amount of accumulated particulate matter, which is collected by the filter, on the basis of an electrostatic capacity between the first and second electrodes. Those four cells which are disposed adjacent to each other around the partition walls of the center cell and sandwiched between the first diagonal cells and the second diagonal cells are used as measurement cells.

A protruding amount (length) of each of the first electrodes from the associated first diagonal cell may be longer than a protruding amount of each of the second electrodes from the associated second diagonal cell. The first connecting member may have a first fixture hole such that an end of each first electrode extends through the first fixture hole to fix the end of the first electrode. The second connecting member may have a second fixture hole such that an end of each second electrode extends through the second fixture hole to fix the end of the second electrode. The second connecting member may have a through hole such that each first electrode extends through the through hole without contacting the through hole.

An orifice may be provided at the unplugged end of each of the measurement cells to throttle (reduce) the diameter of the fluid passage of the measurement cell concerned.

A blockage member may be provided in the center cell to block or close the fluid passage of the center cell.

The blockage member may extend from the plugged end to the unplugged end of the center cell such that the center cell is filled with the blockage member.

The blockage member may plug (seal) the unplugged end of the cell.

The unplugged ends of the first diagonal cells or the unplugged ends of the second diagonal cells may be closed by second blockage members.

The filter may be disposed in the exhaust passage with the plugged side of the center cell facing toward the upstream side of the exhaust passage.

The particulate matter measuring device may further include a bypass passage that branches off from the exhaust passage at a predetermined position, and a second filter that is provided in the exhaust passage at a position downstream of the predetermined position (branching position of the bypass passage) and that collects particulate matter in the exhaust gas flowing through the exhaust passage downstream of the predetermined position. The filter may be disposed in the bypass passage.

When forced regeneration for burning and removing particulate matter that has accumulated in the filter is executed, the first and second electrodes may function as a heater.

The particulate matter measuring device according to the present invention can optimize the electrode arrangement so as to effectively increase the number of capacitors formed between the electrodes.

BRIEF DESCRIPTION OF THE DRAWINGS

FIGS. 2a and 2b are a set of views showing a DPF of the particulate matter measuring device according to the embodiment of the present invention. Specifically.

FIG. 3a to FIG. 3e are a set of vertical cross-sectional views taken along the lines A1-A1, A2-A2, A3-A3, A4-A4 and A5-A5, respectively, in FIG. 2a.

FIG. 4a to FIG. 4e are a set of horizontal cross-sectional views taken along the lines B1-B1, B2-B2, B3-B3, B4-B4 and B5-B5, respectively, in FIG. 2a.

DETAILED DESCRIPTION

Hereinafter, with reference to FIG. 1 to FIG. 4e, a device for measuring particulate matter according to embodiments of the present invention will be described. Identical parts are given identical reference numerals and symbols, and their names and functions are identical as well. Therefore, detailed descriptions of such parts will not be repeated.

Figure 1:
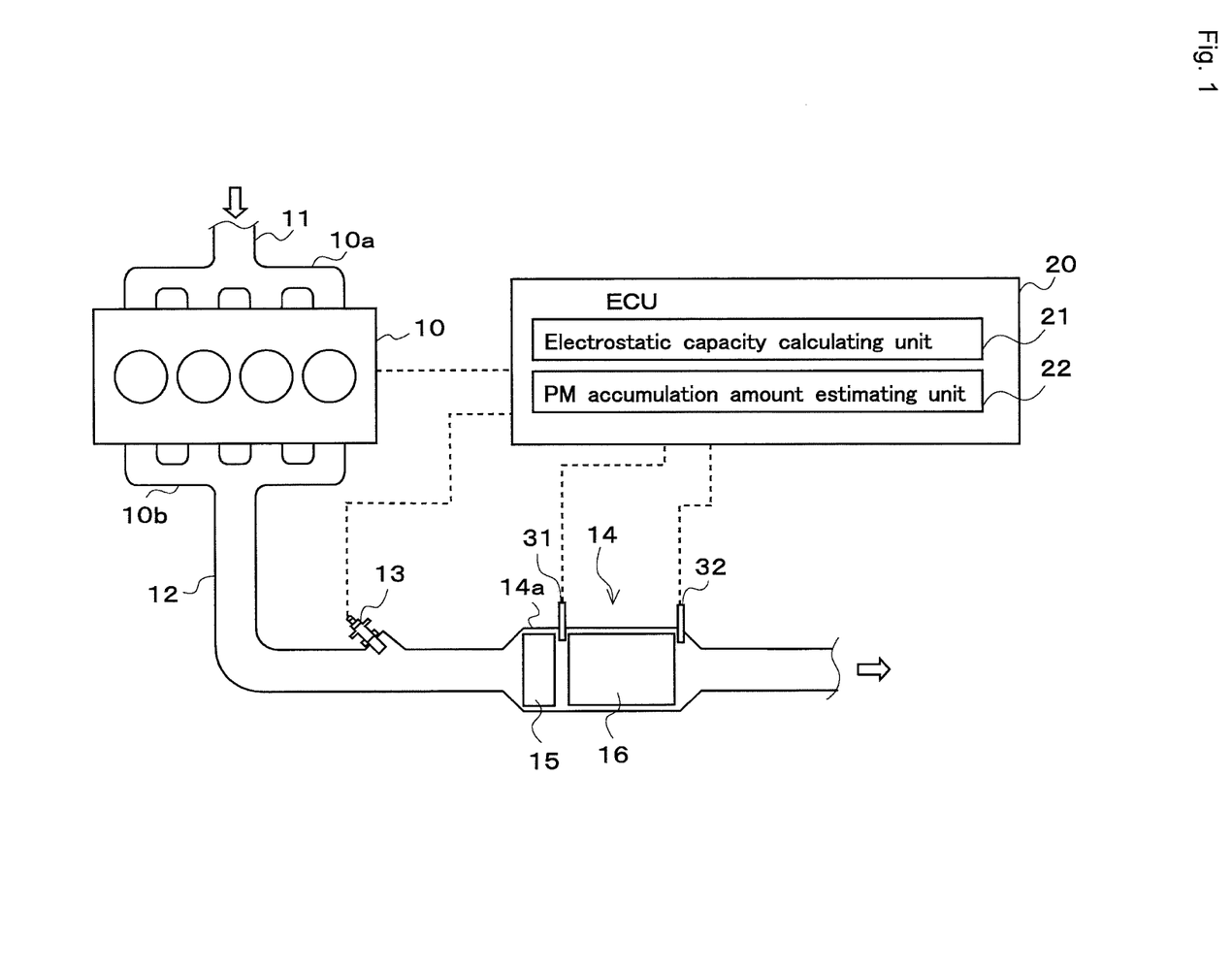
FIG. 1 is an overall configuration diagram schematically illustrating a particulate matter measuring device according to an embodiment of the present invention.

As illustrated in FIG. 1, a diesel engine (hereinafter simply referred to as "engine") 10 has an intake manifold 10a and an exhaust manifold 10b. An intake passage 11 for introducing fresh air is connected to the intake manifold 10a, and an exhaust passage 12 for discharging an exhaust gas to the atmosphere is connected to the exhaust manifold 10b.

An in-pipe injection device 13, an exhaust gas post-treatment device 14, a DPF inlet temperature sensor 31, and a DPF outlet temperature sensor 32 are provided in the exhaust passage 12. The in-pipe injection device 13 is arranged upstream of the exhaust gas post-treatment device 14. The exhaust gas post-treatment device 14 is arranged upstream of the DPF inlet temperature sensor 31. The DPF inlet temperature sensor 31 is arranged upstream of the DPF outlet temperature sensor 32.

The in-pipe injection device 13 injects unburned fuel (primarily HC) into the exhaust passage 12, in response to an instruction signal from an electronic control unit (hereinafter referred to as "ECU") 20. The in-pipe injection device 13 may be omitted if post-injection through multiple-injection of the engine 10 is carried out.

The DPF inlet temperature sensor 31 detects the temperature of the exhaust gas flowing into a DPF 16 (hereinafter referred to as "inlet temperature $T_{IN}$"). The DPF outlet temperature sensor 32 detects the temperature of the exhaust gas flowing out of the DPF 16 (hereinafter referred to as "outlet temperature $T_{OUT}$"). The inlet temperature $T_{IN}$ and the outlet temperature $T_{OUT}$ are introduced to the ECU 20, which is electrically connected to the DPF inlet temperature sensor 31 and the DPF outlet temperature sensor 32.

The exhaust gas post-treatment device 14 is constituted by an oxidation catalyst 15 and the DPF 16 disposed inside a casing 14a. The oxidation catalyst 15 is arranged upstream of the DPF 16.

The oxidation catalyst 15 includes, for example, a ceramic carrier having a cordierite honeycomb structure, with a catalyst component supported on a surface of the ceramic carrier. When forced regeneration of the DPF 16 is carried out, the oxidation catalyst 15 oxidizes the unburned fuel (primarily HC) upon the unburned fuel being supplied by the in-pipe injection device 13 or through post-injection, thereby causing the exhaust gas temperature to rise. Thus, the temperature of the DPF 16 is raised to the PM-burning temperature (e.g., approximately 600 degrees C.), and the accumulated PM is burned and removed.

The DPF 16 includes, for example, a number of cells arranged along the flowing direction of the exhaust gas. The cells form lattice-patterned exhaust flow channels defined by partition walls. The partition walls are made from porous ceramics. The cells are plugged alternatingly at their upstream sides (upstream ends) and their downstream sides (downstream ends). Referring to FIG. 2a to FIG. 4e, the structure of the DPF 16 of this embodiment will be described in detail.

As illustrated in FIG. 2a to FIG. 4e, a plurality of cells 1 that are plugged at the upstream side of the exhaust passage are selected as center cells in the DPF 16. Blockage members 6 are provided in the center cells 1. A pair of cells 2 are disposed diagonally across each of the center cells 1, and first electrodes A are received in the respective cells 2 (hereinafter, the cells 2 are referred to as "first-electrode cells"). Another pair of cells 3 are disposed diagonally across each of the center cells 1, and second electrodes B are received in the respective cells 3 (hereinafter, the cells 3 are referred to as second-electrode cells).

Figure 2A:
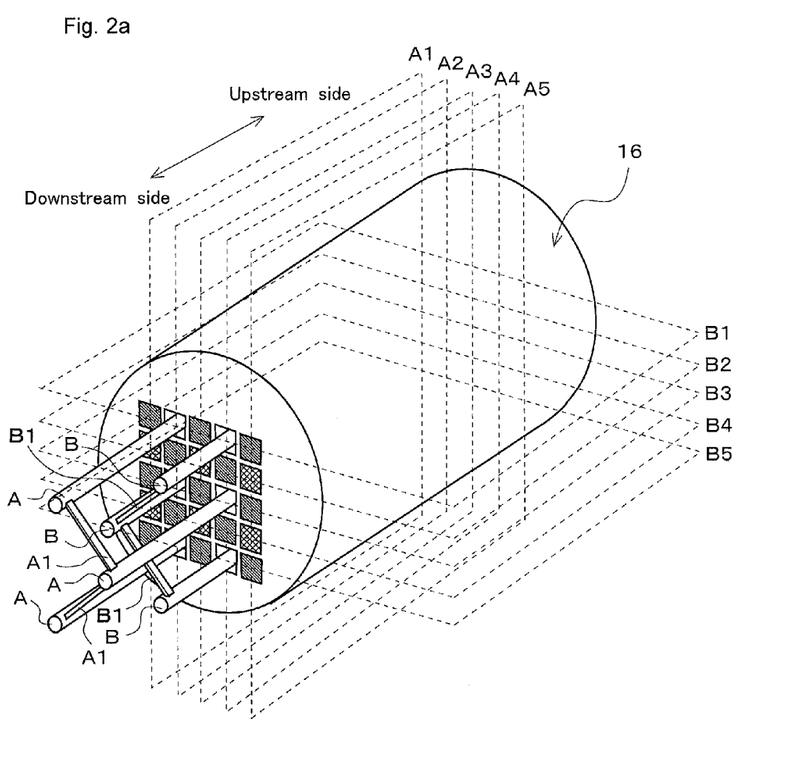
FIG. 2a is a schematic perspective view of the DPF as viewed from the downstream side of the exhaust passage.
Figure 2B:
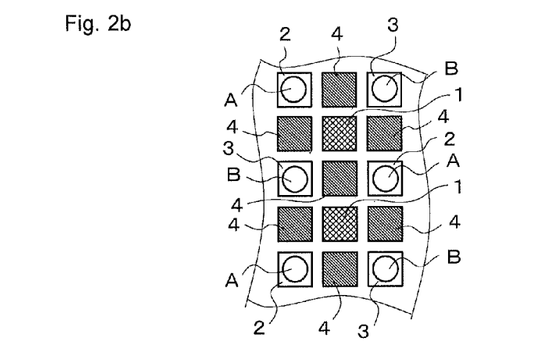
FIG. 2b is a schematic plan view of part of the DPF as viewed from the downstream side of the exhaust passage.
Figure 3A:
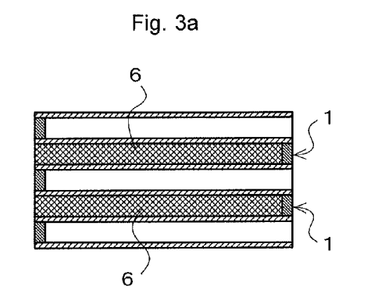
Figure 3B:
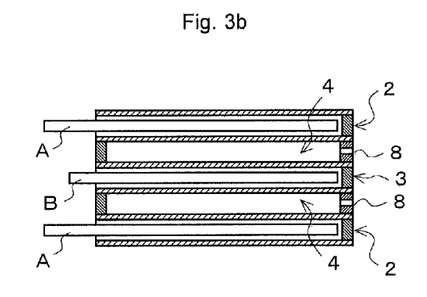
Figure 3C:
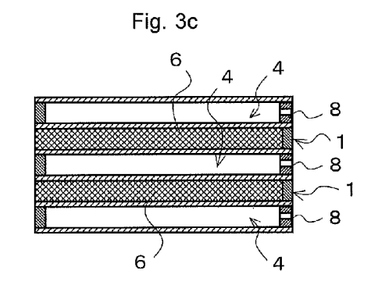
Figure 3D:
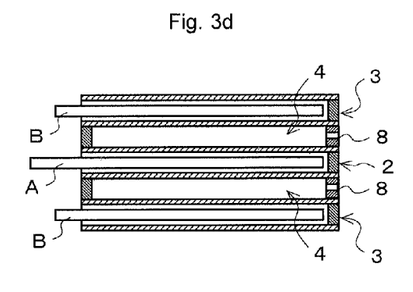
Figure 3E:
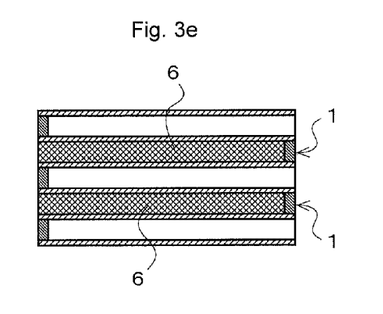
Figure 4A:
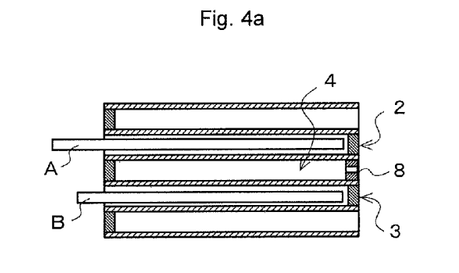
Figure 4B:
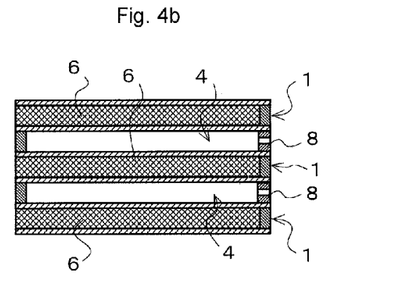
Figure 4C:
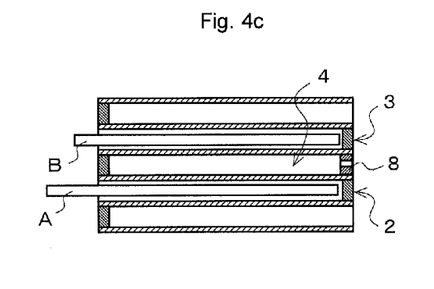
Figure 4D:
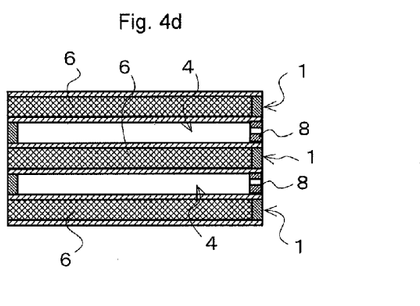
Figure 4E:
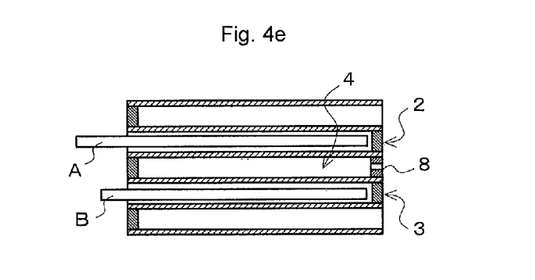

The first electrodes A and the second electrodes B are made from, for example, conductive metal wires. The first electrodes A are received in the first-electrode cells 2 from the unplugged side (their downstream ends in the flow direction of the exhaust gas), and the second electrodes B are received in the second-electrode cells 3 from the unplugged side, respectively. Thus, the four electrodes are arranged diagonally across the center cell 1, and four capacitors are formed between the first electrodes A and the second electrodes B. In the following description, the four cells 4 that are situated adjacent to each other around the partition walls of the center cell 1 and sandwiched between the first-electrode cells 2 and the second-electrode cells 3 are referred to as "measurement cells."

The first electrodes A received in the first-electrode cells 2 have their end portions protruding outward on the downstream side of the exhaust passage, and these end portions are connected to each other by a first connecting member A1 (see FIG. 2*a*) made from a conductive metal wire. In a similar manner, the second electrodes B received in the second-electrode cells 3 have their downstream end portions protruding outward on the downstream side of the exhaust passage, and these end portions are connected to each other by a second connecting member B1 (see FIG. 2*a*) made from a conductive metal wire.

In this embodiment, a protruding amount (length) of the first electrode A is greater than a protruding amount (length) of the second electrode B in order to prevent the first connecting member A1 and the second connecting member B1 from coming into contact with each other. It should be noted, however, that the protruding amount of the first electrode A need not be greater than the second electrode B, i.e., the protruding length of the second electrode B may be greater than the protruding length of the first electrode A.

Figure 5:
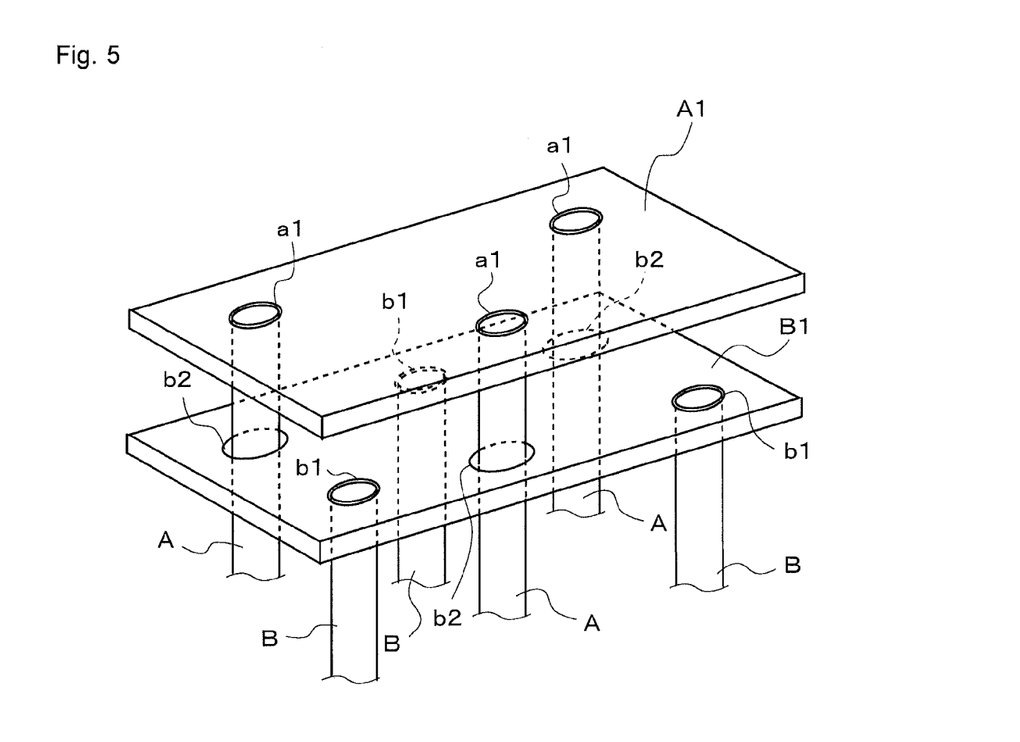
FIG. 5 is a schematic perspective view of modified connecting members in the particulate matter measuring device according to an embodiment of the present invention.
Figure 6A:
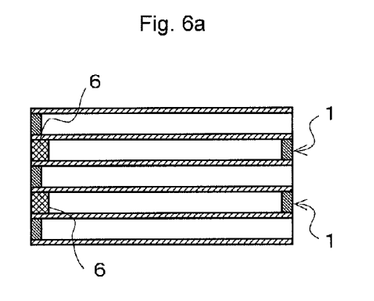
FIGS. 6a to 6e are a set of schematic cross-sectional views of modified blockage members in the particulate matter measuring device according to an embodiment of the present invention.
Figure 6B:
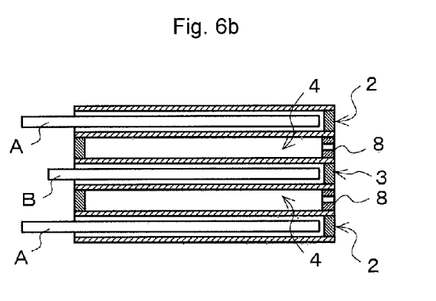
Figure 6C:
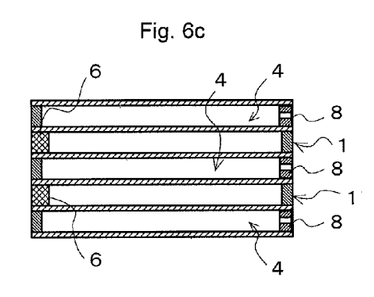
Figure 6D:
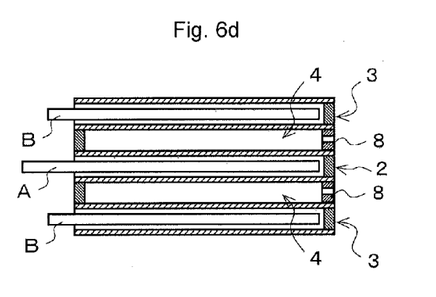
Figure 6E:
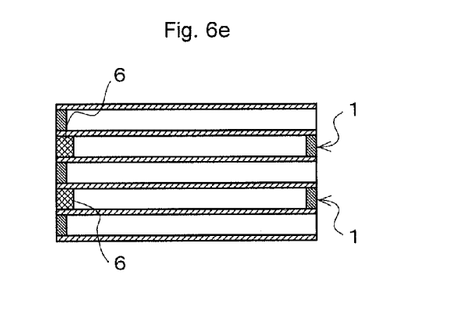
Figure 7A:
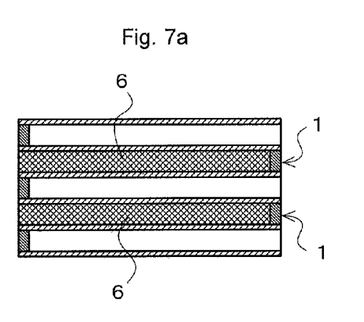
FIGS. 7a to 7e are a set of schematic cross-sectional views of modified electrode cells in the particulate matter measuring device according to an embodiment of the present invention.
Figure 7B:
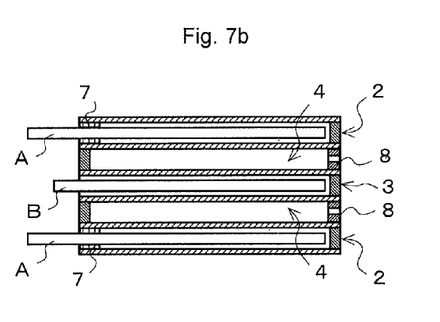
Figure 7C:
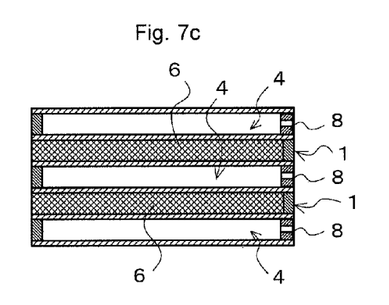
Figure 7D:
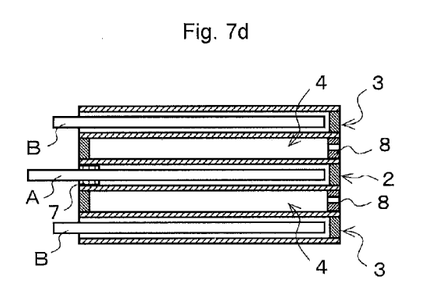
Figure 7E:
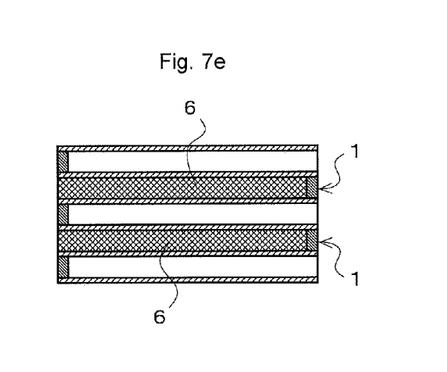

As shown in FIG. 5, each of the first connecting members A1 and the second connecting members B1 may have a flat plate shape. In this configuration, the first connecting A1 may have a fixture hole a1 such that an end of the first electrode A extends through the fixture hole a1 and is secured by welding, and the second connecting B1 may have a fixture hole b1 such that an end of the second electrode B extends through the fixture hole b1 and is secured by welding. The second connecting member B1 may have a through hole b2 that has a larger diameter than the first electrode A such that the first electrode A can extend through the through hole b2 without contacting the through hole b2.

An orifice 8 is provided at the upstream end of the measurement cell 4 to throttle the exhaust gas flowing into the measurement cell 4 (see FIGS. 3*a*-3*e* and FIGS. 4*a*-4*e*). The "upstream end" is the end positioned upstream in terms of the flow direction of the exhaust gas. The orifice 8 reduces a flow rate of the exhaust gas flowing into the measurement cell 4, and therefore it is possible to delay the accumulation of PM on the partition walls of the measurement cell 4. As such, if the opening diameter of the orifice 8 is set to an optimal value under given conditions, it is possible to adjust the timing of saturation of the changing electrostatic capacity between the first electrode A and the second electrode B to desired timing.

A blockage member 6 for blocking (closing) the exhaust passage is provided in each of the center cells 1. For example, the blockage member 6 is made from ceramics, which is the same material as the DPF 16. In this embodiment, the blockage member 6 extends from the plugged end to the unplugged end of the center cell 1 such that the blockage member 6 closes the entire exhaust passage inside the center cell 1, and the entire interior of the center cell 1 is filled with the blockage member 6 (see FIGS. 3*a*-3*e* and FIGS. 4*a*-4*e*).

Accordingly, the exhaust gas flowing into the measurement cell 4 does not flow into the center cell 1, but flows into the first-electrode cells 2 and the second-electrode cells 3. Thus, the PM in the exhaust gas flowing into the measurement cell 4 is collected (retained) on the surfaces of the partition walls of the electrode cells 2 and 3. The accumulation of PM on the partition walls on the center cell 1 side is effectively suppressed. In particular, due to the synergetic effect with the orifice 8, it is possible to effectively reduce not only the accumulation of PM on the partition walls of the measurement cell 4 on the center cell side, but also on a turned U-shaped (U-shaped) accumulation of PM on the rear face of the plug and the partition walls in the measurement cell 4.

It should be noted that the entire interior of the center cell 1 may not be filed with the blockage member 6. As shown in FIGS. 6*a*-6*e*, the blockage member 6 may be provided to block part of the fluid passage in the center cell 1. In the illustrated embodiment, the unplugged end is blocked (closed) by the blockage member 6.

It should also be noted that as shown in FIGS. 7*a*-7*e*, an additional blockage member 7 (second blockage member) may be provided at the open end (insertion opening) of each of the first electrodes A or each of the second electrodes B. In the illustrated embodiment, the additional blockage members 7 are provided in the first electrodes A. In this configuration, it is possible to effectively suppress the accumulation of PM on not only the partition wall surfaces on the center cell 1 side but also on the partition wall surfaces on the first-electrode cells 2 side.

Referring back to FIG. 1, the ECU 20 of this embodiment will be described. The ECU 20 controls fuel injection and other operations of the engine 10 and the in-pipe injection device 13, and includes a known CPU, ROM, RAM, input port, output port, and so on. The ECU 20 includes, as part of its functional elements, an electrostatic capacity calculating unit 21 and a PM accumulation amount estimating unit 22. The description continues with a premise that these functional elements are included in the ECU 20, which is an integrated piece of hardware, but some of these functional elements can be provided in a separate piece of hardware.

The electrostatic capacity calculating unit 21 calculates an electrostatic capacity (capacitance) C between the first electrode A and the second electrode B on the basis of signals from the first electrode A and the second electrode B. The electrostatic capacity C is calculated by the following Expression 1, where c represents a dielectric constant of a medium between the electrodes A and B, S represents the area of the electrodes A and B, and d represents the distance between the electrodes A and B.

$$C = \varepsilon \times \frac{S}{d} \qquad \text{Expression 1}$$

The PM accumulation amount estimating unit 22 estimates the amount $PM_{DEP}$ of accumulated PM collected by the DPF 16, on the basis of the electrostatic capacity C calculated by the electrostatic capacity calculating unit 21 and an average of the inlet temperature $T_{IN}$ detected by the DPF inlet temperature sensor 31 and the outlet temperature $T_{OUT}$ detected by the DPF outlet temperature sensor 32 (hereinafter referred to as "DPF average temperature $T_{AVE}$"). The amount $PM_{DEP}$ of accumulated PM can be estimated by using an approximation formula, a map, or the like obtained or prepared in advance through an experiment.

Operations and advantages of the particulate matter measuring device of this embodiment will now be described.

In the conventional PM sensor, one capacitor is only formed by a pair of electrodes disposed with a single cell interposed therebetween (e.g., only two capacitors are formed by two electrodes A and two electrodes B). Therefore, in order to increase the number of measurement cells, the number of electrodes needs to be increased, and problems arise, i.e., the fabrication cost increases and the PM collection performance of the DPF drops due to an increase in the number of electrode cells.

On the contrary, in the particulate matter measuring device of this embodiment, the two first electrodes A are received in the corresponding pair of cells 2 located diagonally across the center cell 1, the two second electrodes B are disposed in the corresponding pair of cells 3 located diagonally across the center cell 1, and four capacitors are formed between the two first electrodes A and the two second electrodes B. In other words, four cells located diagonally across the center cell 1 serve as the measurement cells for measuring the electrostatic capacity.

Therefore, according to the particulate matter measuring device of this embodiment, a large number of capacitors can be formed effectively without significantly increasing the number of the electrodes A and B, and an increase in the fabrication cost and a decrease in the PM collecting capability of the DPF can effectively be suppressed.

In the conventional PM sensor, the upstream ends of the four cells opposing each other over the measurement cells are only plugged, and their downstream ends are not plugged. Thus, the PM in the exhaust gas flowing into each measurement cell accumulates in a substantially rectangular shape on the surfaces of the partition walls of the measurement cell. If the PM accumulates in the substantially rectangular shape on the partition wall surfaces of the measurement cell in this manner, the electrostatic capacity between the electrodes of the capacitor becomes a saturated condition in a short time (quickly). This results in a problem, i.e., the sensitivity of the capacitor drops.

On the contrary, in the particulate matter measuring device of this embodiment, the orifice 8 is provided at the upstream end of each measurement cell 4 to reduce the flow rate of the exhaust gas. In addition, the blockage member 6 is provided in the center cell 1 to block (close) the exhaust passage inside the center cell 1.

Figure 8:
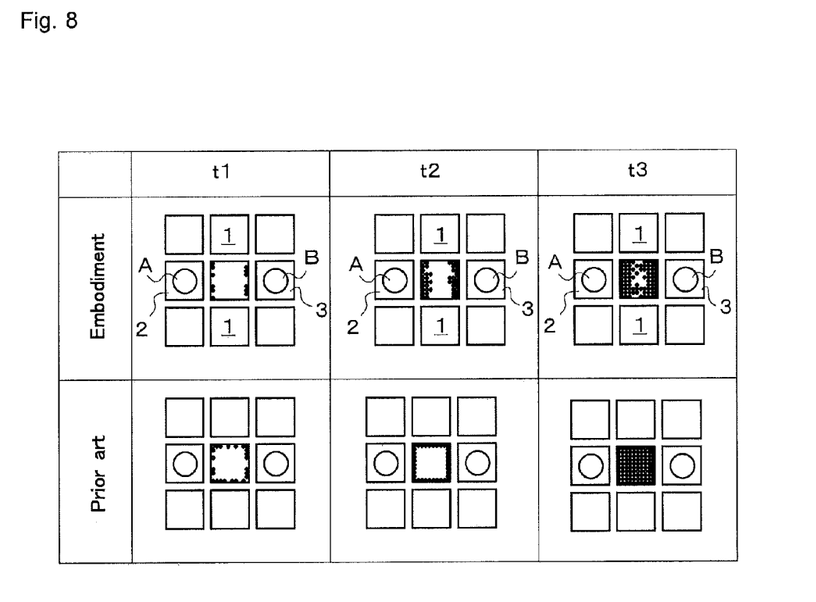
FIG. 8 is a diagram that shows PM accumulated on the surfaces of the partition walls of the measurement cells, as compared to a conventional technology.
Figure 9:
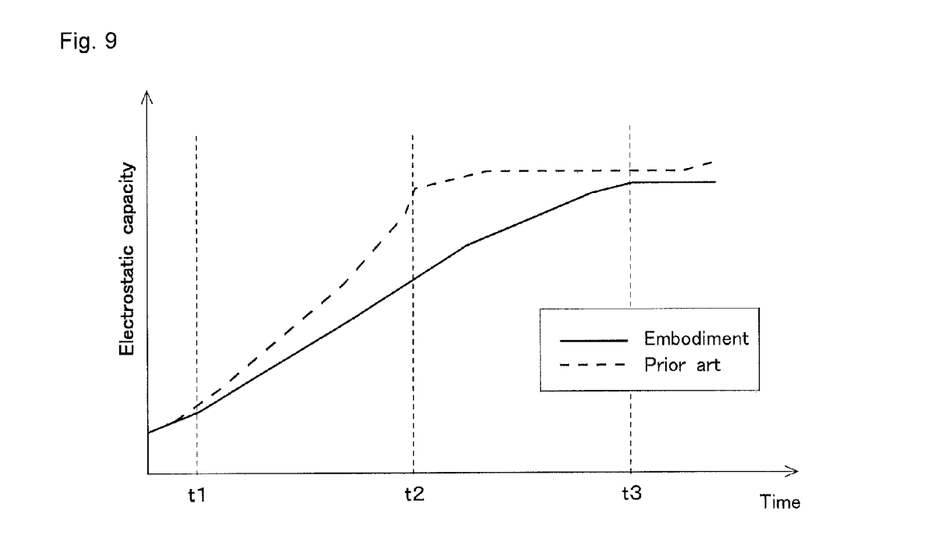
FIG. 9 is a diagram that shows the change of the electrostatic capacity over time until saturation in the particulate matter measuring device according to an embodiment of the present invention, as compared to a conventional technology.

As such, the flow rate of the exhaust gas flowing into the measurement cell 4 is reduced by the orifice 8, and therefore the PM accumulation on the partition walls of the measurement cell 4 is reduced. Also, the flow of the exhaust gas into the center cell 1 is blocked by the blockage member 6, and therefore the PM accumulation on the partition walls on the center cell side is reduced (see FIG. 8). Furthermore, the synergetic effect of the orifice 8 and the blockage member 6 effectively suppresses the PM accumulation on not only the partition walls of the measurement cell 4 on the center cell side, but also on the rear face of the plug and the turned U-shaped (U-shaped) accumulation of PM on the partition wall surfaces inside the measurement cell 4. As a result, as shown in FIG. 9, it is possible to significantly delay the timing of saturation of the changing electrostatic capacity, as compared to the conventional PM sensor.

Therefore, the particulate matter measuring device of this embodiment can effectively prevent the early saturation of the changing electrostatic capacity and reliably prevents the deterioration of the sensitivity.

It is to be noted that the present invention is not limited to the above-described embodiment, and can be implemented with changes and modifications, as appropriate, within the scope that does not depart from the spirit of the present invention.

For example, although the DPF 16 is disposed in the exhaust passage 12 with the plugged sides of the center cells 1 facing toward the upstream side of the exhaust passage in the foregoing description, the DPF 16 may be disposed with the unplugged sides of the center cells 4 facing toward the upstream side of the exhaust passage. It should also be noted that the blockage members 6 in the center cells 1 may be dispensed with, if the orifices 8 alone can adjust the saturation timing of the electrostatic capacity to desired timing.

Figure 10:
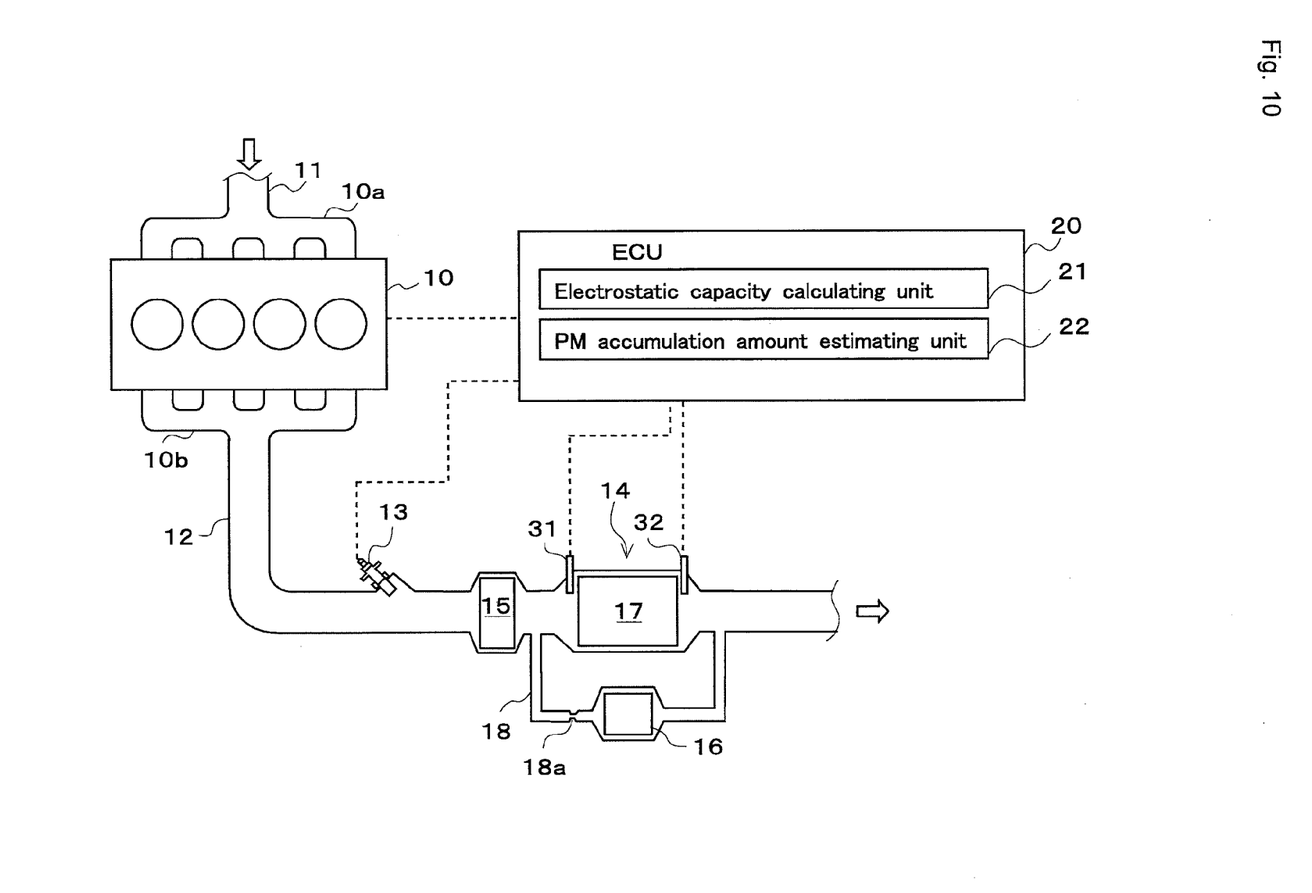
FIG. 10 is an overall configuration diagram schematically illustrating a particulate matter measuring device according to another embodiment of the present invention.

As illustrated in FIG. 10, a bypass passage 18 that branches off from the exhaust passage 12 at a position downstream of the oxidation catalyst 15 may be provided, and a measurement DPF 16 having a reduced capacity may be disposed in the bypass passage 18. In this case, it is preferred that a DPF 17 (second filter) having a large capacity be provided in the exhaust passage 12 downstream of the branching portion, and an orifice 18a for adjusting the flow rate of the exhaust gas be provided in the bypass passage 18. When forced regeneration of the measurement DPF 16 is executed, the electrodes A and B may function as a heater by applying a voltage across the electrodes A and B.

What is claimed is:
1. A device for measuring particulate matter, comprising:
a filter that is provided in an exhaust passage of an internal combustion engine or position and that includes a plurality of cells forming lattice-patterned exhaust flow channels defined by porous partition walls, the plurality of cells being plugged alternatingly at an upstream side and a downstream side;
a pair of first electrodes received in a pair of first diagonal cells out of said plurality of cells, said pair of first diagonal cells disposed diagonally across at least one cell out of said plurality of cells, said at least one cell serving as a center cell, said pair of first electrodes being received from unplugged sides of said pair of first diagonal cells;
a pair of second electrodes received in a pair of second diagonal cells out of said plurality of cells, said pair of second diagonal cells disposed diagonally across the center cell, said pair of second electrodes being received from unplugged sides of said pair of second diagonal cells, the first electrodes being not received in the pair of second diagonal cells;
a first connecting member configured to connect the pair of first electrodes to each other;
a second connecting member configured to connect the pair of second electrodes to each other; and
an accumulation amount calculating unit configured to calculate an amount of accumulated particulate matter collected by the filter, based on an electrostatic capacity between the first and second electrodes,
four cells out of said plurality of cells, which are disposed adjacent to each other around the partition walls of the center cell and sandwiched between the first diagonal cells and the second diagonal cells, being used as measurement cells.

2. The device for measuring particulate matter according to claim 1, wherein a protruding length of each of the first electrodes from the associated first diagonal cells is longer than a protruding length of each of the second electrodes from the associated second diagonal cells,
the first connecting member has a pair of first fixture holes such that an end of each of said first electrodes extends through a respective first fixture hole of the pair of first fixture holes to fix the ends of the first electrodes concerned, and
the second connecting member has a pair of second fixture holes such that an end of each of said second electrodes extends through a respective second fixture hole of the pair of second fixture holes to fix the ends of the second electrodes concerned, and also has a pair of through holes such that each of said first electrodes extend through a respective through hole of the pair of through holes without contacting the respective through hole.

3. The device for measuring particulate matter according to claim 2 further comprising an orifice provided at an unplugged end of each of the measurement cells to reduce a diameter of a fluid passage of the measurement cell concerned.

4. The device for measuring particulate matter according to claim 2 further comprising a blockage member provided in the center cell to close a fluid passage of the center cell.

5. The device for measuring particulate matter according to claim 2, wherein the filter is disposed in the exhaust passage with a plugged side of the center cell facing toward the upstream side.

6. The device for measuring particulate matter according to claim 1 further comprising an orifice provided at an unplugged end of each of the measurement cells to reduce a diameter of a fluid passage of the measurement cell concerned.

7. The device for measuring particulate matter according to claim 6 further comprising a blockage member provided in the center cell and configured to close a fluid passage of the center cell.

8. The device for measuring particulate matter according to claim 6, wherein the filter is disposed in the exhaust passage with a plugged side of the center cell facing toward the upstream side.

9. The device for measuring particulate matter according to claim 1 further comprising a blockage member provided in the center cell and configured to block a fluid passage of the center cell.

10. The device for measuring particulate matter according to claim 9, wherein the blockage member extends from a plugged end to an unplugged end of the center cell such that the center cell is filled with the blockage member.

11. The device for measuring particulate matter according to claim 10 further comprising second blockage members configured to close unplugged ends of the first diagonal cells or unplugged ends of the second diagonal cells.

12. The device for measuring particulate matter according to claim 10, wherein the filter is disposed in the exhaust passage with a plugged side of the center cell facing toward the upstream side.

13. The device for measuring particulate matter according to claim 9, wherein the blockage member closes the unplugged end of the cell.

14. The device for measuring particulate matter according to claim 13 further comprising second blockage members configured to close unplugged ends of the first diagonal cells or unplugged ends of the second diagonal cells.

15. The device for measuring particulate matter according to claim 13, wherein the filter is disposed in the exhaust passage with a plugged side of the center cell facing toward the upstream side.

16. The device for measuring particulate matter according to claim 9 further comprising second blockage members configured to close unplugged ends of the first diagonal cells or unplugged ends of the second diagonal cells.

17. The device for measuring particulate matter according to claim 9, wherein the filter is disposed in the exhaust passage with a plugged side of the center cell facing toward the upstream side.

18. The device for measuring particulate matter according to claim 1, wherein the filter is disposed in the exhaust passage with a plugged side of the center cell facing toward the upstream side.

19. The device for measuring particulate matter according claim 1, further comprising:
a second filter that is provided in the exhaust passage at a position downstream of the predetermined position and configured to collect particulate matter in the exhaust gas flowing through the exhaust passage downstream of the predetermined position,
wherein the filter is disposed in the bypass passage.

20. The device for measuring particulate matter according to claim 19, wherein when forced regeneration for burning and removing the particulate matter that has accumulated in the filter is executed, the first and second electrodes function as a heater.

* * * * *